US005656310A

United States Patent [19]
Santillo, Jr.

[11] Patent Number: 5,656,310
[45] Date of Patent: Aug. 12, 1997

[54] PROCESS FOR PRODUCING A POWDERED FOOD SUPPLEMENT

[76] Inventor: Humbart D. Santillo, Jr., 5010 Glenwood Dr., Williamsville, N.Y. 14221

[21] Appl. No.: 955,919

[22] Filed: Oct. 2, 1992

[51] Int. Cl.$^6$ .......................................... A23L 1/28
[52] U.S. Cl. .................. 426/61; 426/63; 426/599; 426/640; 426/800; 426/801
[58] Field of Search ..................... 426/590, 595, 426/599, 61, 63, 800, 801, 615, 640

[56] References Cited

U.S. PATENT DOCUMENTS

| | | | |
|---|---|---|---|
| 1,204,880 | 11/1916 | Kern | 426/590 |
| 1,204,881 | 11/1916 | Kern | 426/590 |
| 3,433,644 | 3/1969 | Ganske et al. | 426/590 |
| 3,615,674 | 10/1971 | Johnston | 426/590 |
| 3,615,721 | 10/1971 | Silberman | 426/52 |
| 4,233,334 | 11/1980 | Owades | 426/590 |
| 4,544,558 | 10/1985 | Pellegrini | 426/52 |
| 4,716,044 | 12/1987 | Thomas et al. | 426/51 |
| 5,096,719 | 3/1992 | Gresch | 426/51 |

*Primary Examiner*—Leslie Wong
*Attorney, Agent, or Firm*—Harris Beach & Wilcox, LLP

[57] ABSTRACT

A process for preparing a food supplement is disclosed. In the first step of this process, at least two different food materials are juiced either together or separately to provide a juice fraction and a fiber fraction. The juice fraction is dried to produce a powder. The fiber fraction is dried. Thereafter, from about 80 to about 98 parts of the dried juice fraction, from about 1 to about 10 parts of the dried fiber fraction, and from about 1 to about 10 parts of a specified mixture of enzymes is mixed to provide the supplement.

13 Claims, 1 Drawing Sheet

5,656,310

PROCESS FOR PRODUCING A POWDERED FOOD SUPPLEMENT

FIELD OF THE INVENTION

A stable, concentrated, powdered food composition which is relatively easy to digest is disclosed.

BACKGROUND OF THE INVENTION

Powdered food compositions are well known to those skilled in the art. Thus, for example, "Tang" is a commercially available powdered, synthetic organic drink.

Digestion is the chemical process by which nutrient molecules are converted within a body to forms usable by the cells. The chemical reactions occurring during digestion are facilitated by enzymes, which are catalysts, usually comprised of protein, which have specific actions and optimum activities at a definite pH value.

Enzymes are produced by the D.N.A. replication process in living beings. There is a substantial amount of evidence indicating that the aging process, in part, results from a reduction in the amount of enzyme produced by a living body. Thus, as is disclosed at page 14 of Humbart Santillo's "Food Enyzmes" (Hohm Press, Prescott, Arizona, 1991), "A further experiment in relation to saliva and its amylase content was performed . . . . Used in this experiment were young adults from the ages of 21 to 31 and another group ranging from age 69 to 100. It was shown that the younger group had 30 times more amylase in their saliva than the elderly group."

There thus is a need for nutritional supplements which, in addition to nutrients, contain enzymes which will facilitate the digestion of the nutrients. It would be especially desirable if such food supplements would contain enzymes which could function in both the stomach and the intestines of a user and which would not be destroyed in the process of digestion.

Most enzymes have an optimum pH value at which they function, and for most enzymes this pH value is in the range of from about 4.5 to about 8.0; see, e.g., page 354 of John M. DeMan's "Principles of Food Chemistry" (Van Nostrand Reinhold Company, New York, N.Y., 1980). It has been said that ". . . the presence of too many hydrogen or hydroxy ions interferes with the conforming shape of the enzymes;" see, e.g., page 44 of Gabrille I. Edwards' "Biology the Easy Way" (Barrons Educational Series, Inc., New York, N.Y., 1990).

The stomach of human beings is comprised of gastric juice, which has a pH of about 1.0. Most enzymes are inactivated in the presence of such an acidic environment; thus, food supplements comprised of such enzymes will not necessarily be readily digested within the stomach.

Proteases are enzymes that split proteins into proteoses and peptones. Many enzymes, which are immune to attack by proteases in one environment, are susceptible to such attack in another environment; and thus many enzymes are destroyed when introduced into a human body.

It is an object of this invention to provide a food supplement which can be stored indefinitely at room temperature while retaining its potency.

It is another object of this invention to provide a food supplement which has substantially greater nutritive value than many of the raw foods from which it is derived.

It is yet another object of this invention to provide a food supplement which can readily be digested at least in part in the stomach of its user.

It is yet another object of this invention to provide a food supplement which furnishes one or more enzymes to the body of its user which are not destroyed during digestion.

SUMMARY OF THIS INVENTION

In accordance with this invention, there is provided a food supplement which contains a mixture of a first plant powder, a second plant powder, fiber, and at least one enzyme derived from the mold genus aspergillus.

BRIEF DESCRIPTION OF THE DRAWING

The invention will be described by reference to the following FIGURE, in which like numerals refer to like elements, and in which.

DESCRIPTION OF THE PREFERRED EMBODIMENT

Figure 1:
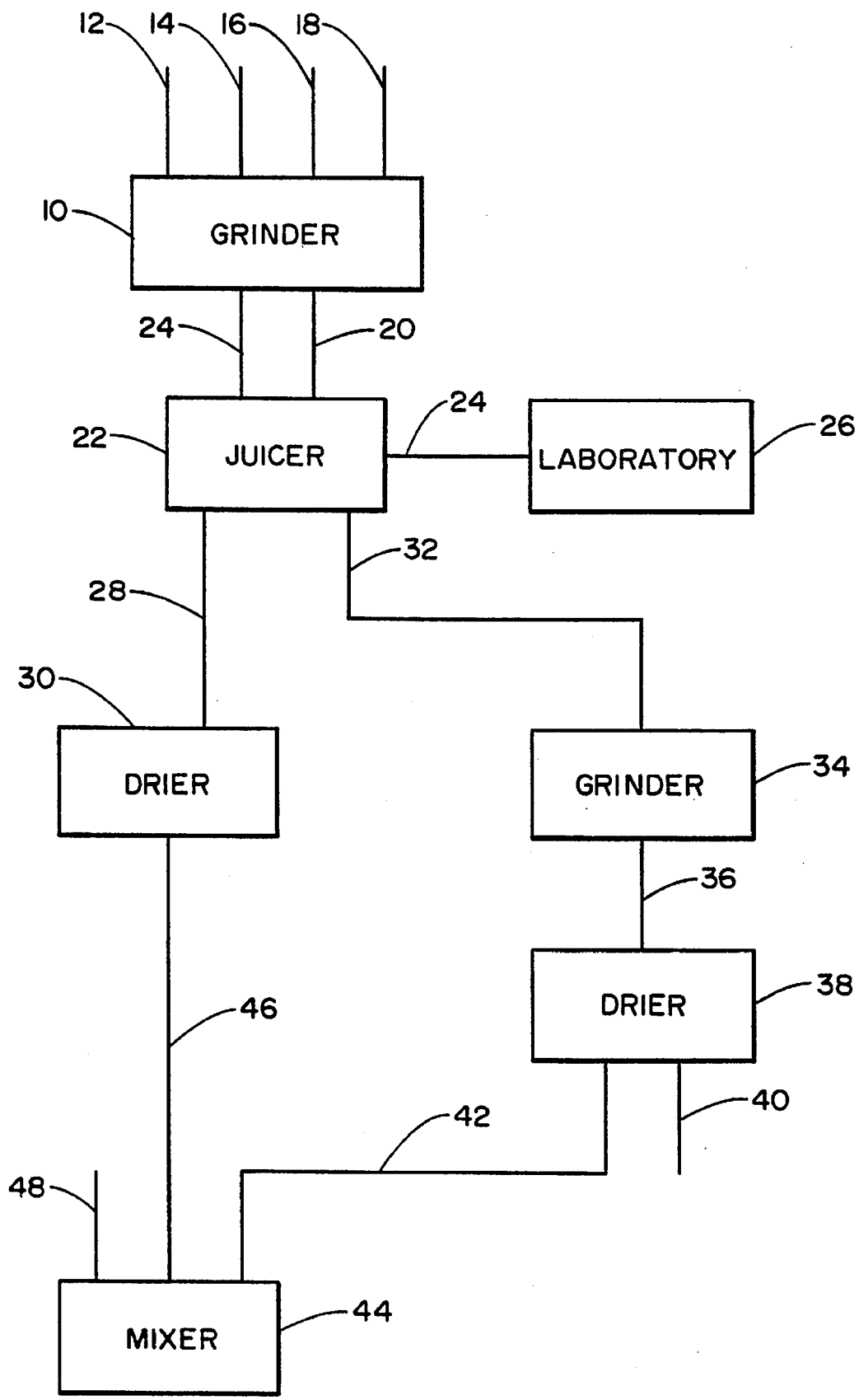
FIGURE 1 is a flow diagram of a preferred process for making the composition of this invention.

FIGURE 1 is a flow diagram of one preferred embodiment of the process of applicant's invention. Referring to FIGURE 1, it will be seen that, to grinder 10 is charged at least two different vegetable and/or fruit materials.

Different combinations of vegetable materials, and/fruit materials, may be charged to mixer 10 via lines 12 and/or 14 and/or 16 and/or 18. It is preferred that at least two different such materials be charged. It is more preferred that at least three different such materials be charged. In one embodiment, at least four such different materials are charged.

In one embodiment, suitable for administration to children, pineapples, apples, strawberries, and oranges are charged to the grinder 10. In one aspect of this embodiment, four of pineapple, three parts of apples, one part of oranges, and one part of strawberries are charged to the mixer.

In another embodiment, which is suitable for administration to athletes, carrots, apples, kale, watercrest, beets, beet tops, and alfalfa are charged to mixer 10.

In yet another embodiment, which is suitable for weight loss diets, cucumbers, lettuce, apples, carrots, and dandelions are charged to mixer 10.

In yet another embodiment, parsley, kale, spinach, chard, apples, carrots, and beet tops are charged to mixer 10.

In yet another embodiment, algae, parsley, carrots, apples, kale, and alfalfa are charged to mixer 10.

In yet another embodiment, kale, watercrest, celery, carrots, and apples are charged to mixer 10.

In yet another embodiment, cabbage, broccoli, carrots, ginseng, yucca, barley, alfalfa, and carrots are charged to mixer 10.

It is preferred, when a vegetable or fruit is being charged to the mixer 10, to charge the whole vegetable or fruit. In one aspect of this embodiment, not shown, the vegetable(s) and/or fruit(s) is first cleaned prior to being charged to mixer 10.

Any conventional cleaning means may be used to clean the fruits and/or vegetables. Thus, e.g., the fruits and/or vegetables may be cleaned with water. Thus, e.g., the fruits and/or vegetables may be cleaned with solution of hydrogen peroxide.

When apple is one of the components charged to mixer 10, it is preferred that at least about 30 weight percent of the material charged to mixer 10 be comprised of said apples.

When both apples and carrots are charged to mixer 10, it is preferred that they comprise at least about 70 weight percent of the total fruit and vegetable material charged to said mixer.

When a green vegetable material (such as parley, and/or kale and/or spinach and/or endive and/or dandelion) is charged to mixer 10, it is preferred that the total amount of green vegetable material so charged be less than about 15 weight percent of the total amount of vegetable and/or fruit material charged to the mixer 10.

In one embodiment, where the materials charged to mixer 10 are all fruits, dextran is also charged to the mixer. As is known to those skilled in the art, dextran is a gummy, fermentable carbohydrate from growths of *Leucoonstoc mesenteroides* on sucrose. In this embodiment, it is preferred to use at least 50 weight percent of rice dextran, by weight of the total mixture charged to mixer 10.

In one embodiment, it is preferred to grind the vegetable and/or fruit material in grinder 10 so that substantially all of the particles so produced are smaller than about 0.5 inches and, more preferably, than about 0.25 inches. Thereafter, in this embodiment, the material so ground may be passed via line 20 to juicer 22.

In another embodiment, the vegetable and/or fruit material(s) are charged directly to juicer 22 via line 24 without being subjected to a preliminary grinding step. In either event, the vegetable and/or fruit material in juicer 22 is then juiced.

Any juicer suitable for producing both juice and fibrous material from a vegetable and/or fruit material may be used as juicer 22.

The vegetable and/or fruit material charged to grinder 10 is juiced by conventional means. Thus, by way of illustration and not limitation, one may juice said materials by means of the extractor 2 and/or the screw press which are disclosed in U.S. Pat. No. 3,975,546 of Stahmann, the disclosure of which is hereby incorporated by reference into this specification.

Thus, by way of further illustration, one may juice the vegetable and/or fruit material by means of the diffuser or extractor 1 disclosed in U.S. Pat. No. 4,544,558 of Pellegrini, the disclosure of which is also incorporated by reference into this specification.

By way of yet further illustration, U.S. Pat. No. 4,716,044 of Thomas et al. discloses a process for obtaining juice from fruit in which a pumpable fluid puree of fruit and juice is first provided. The disclosure of this patent also is incorporated by reference into the specification.

In another embodiment, the juicing is conducted by means of centrifugation. In yet another embodiment, the juicing is conducted by means of augurs. In yet another embodiment, one may use commercially available juicers.

Thus, by way of further illustration, one may use the juicer sold by Trillium, Inc. of Seattle, Wash. as "The Juiceman Juicer."

The vegetable and/or fruit material in juicer is juiced until at least about 65 weight percent of the juice present in the vegetable and/or fruit material has been extracted. It is preferred to juice such material until at least about 70 weight percent of the juice has been extracted. It is even more preferred to juice said material until at least about 75 weight percent of the juice has been extracted.

One may readily determine the extent of the juicing process by taking a sample of the vegetable and/or fruit material charged to juicer 22, weighing it prior to drying, and drying it so that it contains less than about 0.1 weight percent of moisture. The difference in weight between the undried and the dried sample will be substantially equal to the amount of juice in the vegetable and/or fruit material. Thereafter, during the juicing process, one may periodically withdraw samples of the material being juiced from juicer 22 via line 24 and, in laboratory 26, thereafter determine the amount of juice in the withdrawn samples. When the amount of juice in the withdrawn sample is less than about 25 percent of the total amount of juice originally in the sample, the juicing operation may be stopped.

In general, at least about fifty weight percent of the vegetable and/or fruit material in juicer 22 is comprised of juice, and often at least about 75 weight percent of such material is comprised of juice.

Two different fractions are removed from juicer 22. A juice fraction is passed via line 28 to drier 30. A fiber fraction is passed via line 32 to grinder 34.

The juice fraction generally contains less than about 1.0 weight percent of cellulose. As is known to those skilled in the art, cellulose is a carbohydrate polymer of beta-glucose residue units with beta-1/4 linkages between glucose units; see, e.g., pages 159–162 of said "Principles of Food Chemistry" (by John DeMan). The juice fraction is generally comprised of vitamins, minerals, trace minerals, and enzymes.

The fiber fraction, by comparison, generally contains at least about 70 weight percent of cellulose and, generally, at least about 80 weight percent of cellulose. It also often contains pectin, gums, lignins, and the like.

In drier 30, the juice fraction is dried until it contains less than about 5.0 weight percent of liquid. It is preferred to dry said juice fraction so that it contains less than about 1.0 weight percent of such liquid.

Any conventional means of drying the juice fraction may be used. Thus, for example, one may use the drying means disclosed on pages 711–759 of J. M. Coulson et al.'s "Chemical Engineering," Volume 2, Third Edition (Pergamon Press, Oxford, England, 1978).

In one preferred embodiment, the liquid fraction is subjected to spray drying in drier 30 to simultaneously dry it and form dried particles with a particle size distribution such that substantially all of the dried particles are smaller than about 420 microns. In this embodiment, one may use any of the conventional spray drying techniques known to those skilled in the art. Thus, by way of illustration, one may use one or more of the spray driers disclosed on pages 735–750 of said "Chemical Engineering . . . ." text by Coulson et al.

Referring again to FIGURE 1, the fibrous fraction is preferably passed via line 32 to grinder 34, where it preferably is comminuted until substantially all of its particles are smaller than about 420 microns. Thereafter, the powder so comminuted may be passed via line 36 to drier 38 in which the powder is preferably dried until it has a moisture content of less than about 5.0 weight percent. It is preferred to dry the powder so that it has a moisture content of less than about 1.0 weight percent.

A portion of the dried powder from drier 38 may be discarded via line 40. Another portion of such dried powder is passed via line 42 to mixer 44.

To mixer 44 is charged the dried juice extract powder via line 46, the dried fiber extract powder via line 42, and dried enzyme powder via line 48.

It is preferred to charge from about 80 to about 98 weight percent (by total weight of material in mixer 44) of the dried juice extract powder to mixer 44 via line 46. In one embodiment, at least about 90 weight percent of said dried juice extract powder is charged via line 46.

It is preferred to charge from about 1 to about 10 weight percent of the dried fiber extract powder to mixer 44 via line 42. In one embodiment, from about 2 to about 6 weight percent of such dried fiber extract powder is charged. In another embodiment, from about 3 to about 5 weight percent of said dried fiber extract powder is charged.

It is preferred to charge from about 1 to about 10 weight percent of one or more of the enzymes described below to mixer 44 via line 48. In one embodiment, from about 1 to about 5 weight percent of such enzyme(s) is charged to mixer 44.

The enzymes used in applicant's process preferably are produced by a species of *Aspergillus*. As is known to those skilled in the art, *Aspergillus* is a genus of molds, many of which are parasitic.

In one preferred embodiment, the enzyme(s) used is selected from the group consisting of: (1) alpha-amylase, which is classified as a carbohydrase, which is obtained from *Aspergillus oryzae*, and which has I.U.B. (International Union of Biochemists) number 3.2.1.1., (2) protease, which is obtained from *Aspergillus oryzae*, and which has I.U.B. number 3.4.21.14, (3) lipase, which is obtained from *Aspergillus niger*, and which has I.U.B. number 3.1.1.3, (4) cellulase, which is classified as a carbohydrase, which is obtained from *Aspergillus niger*, and which has I.U.B. number 3.2.1.4, and (5) mixtures thereof. As is known to those skilled in the art, these enzymes, and their associated I.U.B. numbers, are described in the "Food Chemicals Codex," 3rd edition (National Academy Press, Washington, D.C., 1981).

These enzymes are commercially available and may be purchased, either singly or in combination, from the National Enzyme Company, Inc., Post Office Box 128, Forsyth, Mo. 65653. Thus, by way of illustration one may purchase "Formula 1" (which contains protease, amylase, lipase, and cellulase enzymes), "Formula 2" (which contains the amylase, protease, lipase, and cellulase enzymes and, in addition, 200 million viable *Lactobacillus acidophilus* organisms per 220 milligrams of composition), "Formula 6" (which contains the amylase, protease, lipase, and cellulase enzymes and, additionally, marshmallow root and rose hips), "Formula 7" (which contains the amylase, lipase, and protease enzymes plus, in addition, safflower petals), "Formula 9" (which contains the protease, amylase, and lipase enzymes and, additionally, alfalfa juice concentrate, parsley leaf, horsetail rush, and rose hips), "Formula 10" (which contains invertase, amylase, protease, lipase, and cellulase enzymes and, additionally, brewers yeast, gotu kola, rose hips, and urea), "Formula 12" (which contains the cellulase, amylase, protease, and lipase enzymes and, additionally, citrus bioflavonoids, burdock root, and organic germanium), "Formula 13" (which contains lipase, amylase, protease, and cellulase enzymes and, in addition, wheat germ, lecithin, and kelp, "Formula 14" (which contains the protease, amylase, lipase, and cellulase enzymes and, in addition, marine organic minerals (kelp), and irish moss, "Formula 15" (which contains protease, amylase, lipase, and cellulase enzymes and, in addition, spirulina plankton, alfalfa juice concentrate, and parsley leaf), "Formula 16" (which contains protease, amylase, and lipase enzymes and, in addition, calcium lactate), "Formula 17" (which contains protease, amylase, and lipase enzymes and, in addition Pau D'Arco, Yellow Dock, Echinacea, Mullein, and Organic Germanium), "Formula 19" (which contains the protease, amylase, and lipase enzymes and, in addition, calcium gluconate and magnesium gluconate), and the like.

In one embodiment, it is preferred to add each of the aforementioned enzymes to mixer 44. It will be understood that, when said enzymes are added and, additionally, other material(s) are also added (such as, e.g., calcium gluconate), only the amount of enzyme(s) added is to be used in calculating the concentration of the enzyme(s).

The enzyme(s) to be added are preferably in dry, powder form and, thus, contain less than about 5.0 weight percent of moisture and, also, have a particle size such that substantially all of their particles are smaller than about 420 microns.

The materials in mixer 44 are preferably dry mixed until a substantially homogeneous mixture is produced. Then it may be used as a whole food nutritional supplement. This supplement has a very long shelf life, retains most of aromas of the materials from which it was made, is easily digestible, and provides an additional source of enzymes to a user which remain in his system after the food material(s) has been digested.

It is to be understood that the aforementioned description is illustrative only and that changes can be made in the ingredients and their proportions, and in the sequence of combinations and process steps, as well as in other aspects of the invention discussed herein, without departing from the spirit and scope of the invention as defined in the following claims.

Thus, for example, in one embodiment, instead of grinding and/or juicing and/or drying all of the vegetable and/or fruit material together, some or all of these steps may be conducted in separate operations, and the products from one or more of such steps may thereafter be combined.

I claim:

1. A process for producing a food supplement, comprising the steps of:
   (a) juicing a first food material and a second different food material, wherein:
   1. each of said first food material and said second food material is independently selected from the group consisting of a vegetable, a fruit, and mixtures thereof;
   2. said juicing produces a liquid fraction and a fiber fraction, wherein said liquid fraction is comprised of less than about 1.0 weight percent of cellulose, and said fiber fraction is comprised of at least about 70 weight percent of cellulose;
   (b) drying said juice fraction until a first dried powder which is comprised of less than about 5.0 weight percent of liquid and all of whose particles are smaller than 420 microns is produced;
   (c) drying said fiber fraction until a second dried material which is comprised of less than about 5.0 weight percent of liquid is produced;
   (d) providing at least three enzymes selected from the group consisting of alpha amylase (I.U.B. number 3.2.1.1), protease (I.U.B. number 3.4.21.14), lipase (I.U.B. number 3.1.1.3), and cellulase (I.U.B. number 3.2.1.4); and
   (e) mixing from about 80 to about 98 parts by weight of said first dried powder, from about 1 to about 10 parts by weight of said second dried material, and from about 1 to about 10 parts by weight of said enzymes to produce said food supplement.

2. The process as recited in claim 1, wherein a third food material and a fourth food material are also juiced to produce said liquid fraction, and wherein each of said third food material and said fourth food material is also independently selected from the group consisting of a vegetable, a fruit, and mixtures thereof.

3. The process as recited in claim 2, wherein each of said first food material, said second food material, said third food material, and said fourth food material is independently selected from the group consisting of vegetables.

4. The process as recited in claim 2, wherein each of said first food material, said second food material, said third food material, and said fourth food material is independently selected from the group consisting of fruits.

5. The process as recited in claim 2, wherein at least one of said first food material, said second food material, said third food material, and said fourth food material is a tuber.

6. The process as recited in claim 2, wherein there is provided at least four enzymes selected from said group consisting of alpha amylase (I.U.B. number 3.2.1.1), protease (I.U.B. number 3.4.21.14), lipase (I.U.B. number 3.1.1.3), and cellulase (I.U.B. number 3.2.1.4), and mixtures thereof.

7. The process as recited in claim 6, wherein said juice fraction is dried by spray drying.

8. The process as recited in claim 7, wherein said second dried material is a powder all of whose particles are smaller than about 420 microns.

9. The process as recited in claim 8, wherein from about 90 to about 98 parts by weight of said first dried powder are mixed with said second material and said enzymes.

10. The process as recited in claim 9, wherein from about 1 to about 5 parts by weight of said enzymes are mixed with said first dried powder and said second dried material.

11. The process as recited in claim 10, wherein from about 2 to about 5 parts by weight of said second dried material are mixed with said enzymes and said first dried powder.

12. The process as recited in claim 11, wherein, prior to the time said first food material, said second food material, said third food material, and said fourth food material are juiced, they are ground until substantially all of their particles are smaller than about 0.25 inches.

13. The process as recited in claim 12, wherein said first dried powder contains less than about 0.1 weight percent of moisture.

\* \* \* \* \*